United States Patent [19]
Mack

[11] 4,345,898
[45] Aug. 24, 1982

[54] FACE BOW

[76] Inventor: Heinz Mack, Südl. Auffahrtsallee, 8000 München 19, Fed. Rep. of Germany

[21] Appl. No.: 294,232

[22] Filed: Aug. 19, 1981

[30] Foreign Application Priority Data

Sep. 2, 1980 [DE] Fed. Rep. of Germany ....... 3032913

[51] Int. Cl.³ .............................................. A61C 19/04
[52] U.S. Cl. ..................................................... 433/73
[58] Field of Search ............................. 433/73, 68, 55

[56] References Cited
U.S. PATENT DOCUMENTS 3,224,096 12/1965 Stuart ..................................... 433/73
4,084,319 4/1978 Dragan ................................... 433/73

Primary Examiner—Robert Peshock
Attorney, Agent, or Firm—Larson and Taylor

[57] ABSTRACT

The invention relates to a face bow serving to transfer jaw models to an articulator in correct relationship to the skull. It consists essentially of two L-shaped side arms which are connected by pivot bearings to a base plate at two oppositely located peripheral pivot points for scissors-like movement, and which can be locked in the overlapping region of the ends of the transverse portions of the L-shaped side arms. The pivot bearings (12,13) are disposed in the respective L-bends (14,15) of the L-shaped side arms (2,3). In the middle between the pivot bearings (12,13), the base plate (16) has a slot (23) whose longitudinal edges (24,25) extend parallel to the longitudinal axis (26) of the face bow (1) and through which projects the locking means (11), passing rotatably but non-slidably through the free ends (8,9) of the transverse portions (5,7) in the overlapping region.

7 Claims, 5 Drawing Figures

FACE BOW

This invention relates to a face bow consisting essentially of two L-shaped side arms which are connected by pivot bearings to a base plate at two oppositely located peripheral pivot points for scissors-like movement, and which can be locked in the overlapping region of the ends of the transverse portions of the L-shaped side arms.

A face bow of this kind is known for example from U.S. Pat. No. 3,218,716. In this case the base plate is disposed at a distance from the transverse portions of the L-shaped side arms, and the locking means, which is situated in the overlapping region of the transverse portions of the L-shaped side arms, is not connected to the base plate. In this arrangement it has been found particularly disadvantageous that when the locking means is unlocked all mechanical guidance is lost. In addition, in an arrangement of this kind of the locking means, relatively great pressure must be applied to the overlapping ends in order to prevent the unintentional displacement of the side arms during the handling of the face bow. Since in addition the pivot bearings are some distance from the locking means, in this known face bow an intensified lever action occurs, so that the additional danger arises that the locking force applied by the locking means can easily be overcome, which also has the consequence that the scissors-like side arms of the face bow can be unintentionally displaced. Moreover, this effect is further intensified by the arrangement of the slot which is disposed at the free end of one of the transverse portions and extends transversely to the longitudinal axis of the face bow, and by which the locking means is guided.

An object of the invention is therefore to provide a face bow which can be locked easily and reliably.

According to the invention this problem is solved in that:

(a) The pivot bearings are disposed in the respective L-bends of the L-shaped side arms, and (b) In the middle between the pivot bearings the base plate is provided with a slot whose longitudinal edges extend parallel to the longitudinal axis of the face bow and through which the locking means projects, said locking means passing rotatably but non-slidably through the free ends of the transverse portions in the overlapping region.

In the face bow according to the invention the pivot bearings are thus moved into the corner regions at the transition point from the longitudinal portions to the transverse portions of the respective side arms, so that the leverage between the locking means and the pivot bearings is substantially reduced. This firstly ensures that an intensification of force during the handling of the face bow, which can lead to the unlocking of the locking means, is to a large extent avoided.

Another very important feature of the invention consists in that the slot through which the locking means projects is not disposed at a free end of a transverse portion of the L-shaped side arm, but is disposed in the base plate, parallel to the longitudinal axis, in the middle between the pivot bearings, and that the locking means passes not only through the free ends of the transverse portions of the L-shaped side arms, but also through the base plate. Reliable spacing of the side arms is achieved in this arrangement with relatively slight locking forces.

It is expedient for the locking means to consist of a locking screw with a corresponding locking nut. In order to ensure the simplest possible manipulation of the locking means, the locking nut is an internally threaded knurled nut engaged on an external thread on a portion of the locking screw. A knurled nut of this kind forms a very useful gripping surface for the displacement of the nut, which can easily be operated by two fingers of one hand. Between the locking nut and the slot it is preferable to dispose a washer, which on the one hand serves to maintain a self-locking action of the screwthread connection during locking and on the other hand also serves the purpose of distributing the holding force applied during locking over a larger area.

According to the invention the base plate is preferably E-shaped. The pivot bearings pass through the end regions of the outer legs of the E, and the slot is situated in the central leg of the E.

The invention is explained below with reference to FIGS. 1 to 5, which illustrates particularly preferred embodiments of the invention, without however restricting the invention thereto. All details which are not mentioned in the description, but which can be seen in the drawings, constitute an integral part of the essential disclosure of the present invention. The references used in the drawings and the appertaining parts of the description are listed at the end of the description.

Figure 3:
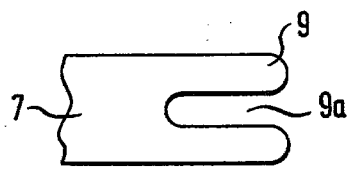

FIG. 3 is a top view of the free end 9 of the transverse portion 7 of the L-shaped side arm 3.

Figure 4:
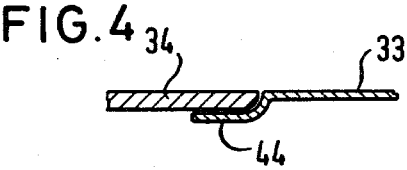

FIG. 4 is a longitudinal section through the bite fork 33 and a part of the bite fork handle 34 with the depression 44.

Figure 5:
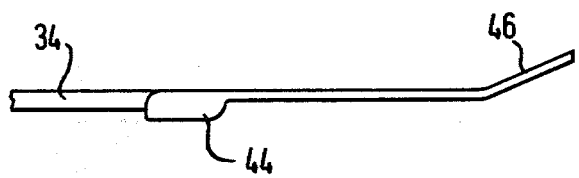

FIG. 5 is a side view of the bite fork with the preferably upwardly curved front region 46.

Figure 1:
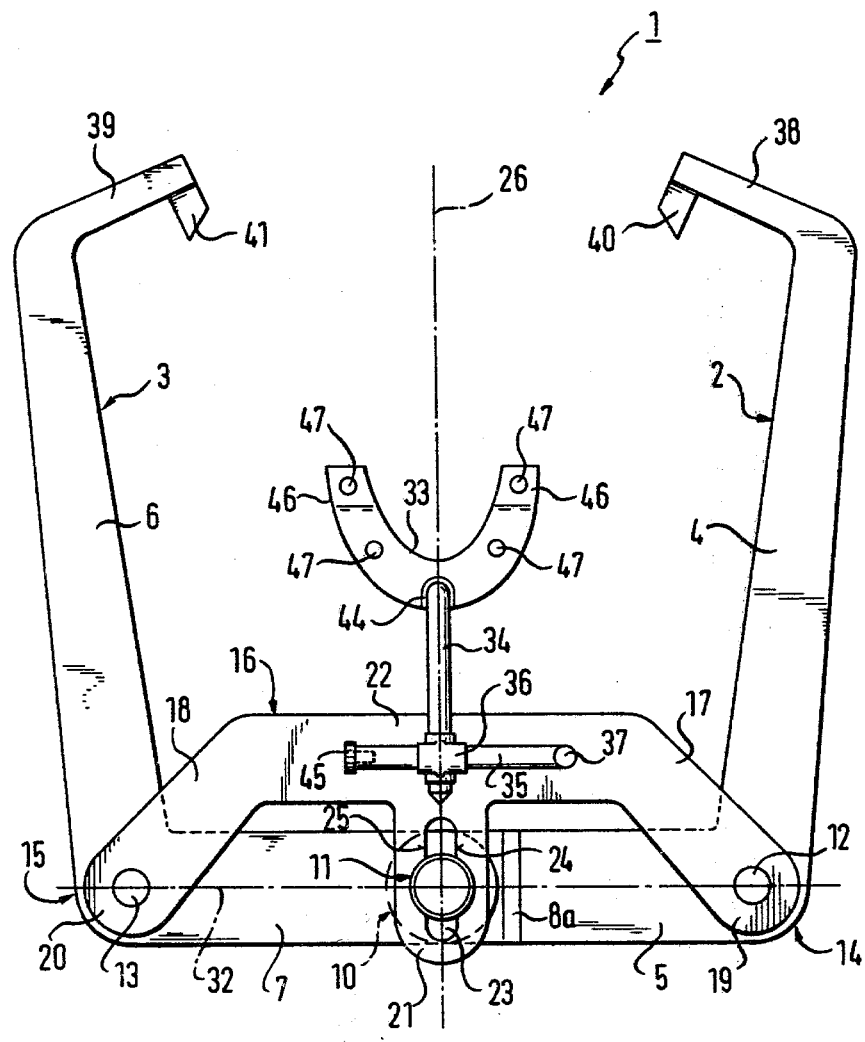
FIG. 1 is a bottom view on a reduced scale of a face bow 1 according to the invention.

In FIG. 1 a preferred embodiment of a face bow is indicated by the general reference 1. The face bow 1 comprises side arms 2 and 3 lying respectively on the right and the left in FIG. 1. Each side arm 2,3 is roughly L-shaped and made in one piece. The L-shaped side arm 2 lying on the right comprises a longitudinal portion 4 and a transverse portion 5 extending approximately at right angles thereto. Similarly, the side arm 3 lying on the left in the face bow 1 comprises a longitudinal portion 6 and a transverse portion 7 extending approximately at right angles thereto. The free ends 8, 9 of the respective transverse portions 5,7 of the side arms 2,3 overlap in a region designated 10. In this region the free end 8 of the transverse portion 5 preferably has a crank 8a, so that parallel overlapping is achieved. In this overlapping region 10 the two side arms 2,3 of the face bow 1 are locked together and to the base plate 16 with the aid of a locking means.

According to the invention the pivot bearings 12,13 for the two side arms 2,3 lie in opposite corner regions 14,15 at the respective transition points from the longitudinal portions 4,6 to the transverse portions 5,7 of the respective L-shaped side arms 2,3. These pivot bearings 12,13 pass through the respective side arms 2,3 in the oppositely positioned corner regions 14,15. In addition, the pivot bearings 12,13 pass through the base plate 16 in the end regions 19,20. In the embodiment illustrated the base plate 16 is preferably of E-shaped construction. The E-shaped base plate is composed of two outer E-legs 17,18, a middle E-leg 21, and a connecting leg 22 joining the E-legs 17,18, and 21. In the embodiment illustrated the pivot bearings 12,13 pass through the end regions 19,20 of the outer E-legs 17,18. The slot 23 is formed in the middle E-leg 21. The outer E-legs 17,18 in the embodiment illustrated extend at an obtuse angle to the connecting leg 22 of the E-shaped base plate 16. The slot 23 has two longitudinal edges 24,25 which extend parallel to one another and parallel to the center axis (designated 26) of the face bow 1, the longitudinal axis 26 bisecting the slot in the longitudinal direction, so that the slot 23 is positioned midway between the two pivot bearings 12,13. When the side arms 2,3 perform a scissors movement, the locking means 11 disposed in the overlapping region 10 is guided in the slot 23. The locking means 11 preferably consists of a locking screw 27 with a corresponding locking nut 30. The locking screw 27 is preferably seated fixedly and non-rotatably in the free end 8 of the transverse portion 5. Without making contact, the locking screw 27 passes through both the free end 9 of the transverse portion 7 and the base plate 16, the free end 9 of the transverse portion 7 preferably having a cutout 9a instead of a hole.

Figure 2:
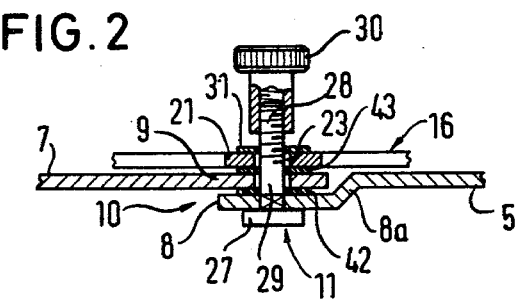
FIG. 2 is a longitudinal section through the locking means 11, along the connecting line 32.

FIG. 2 shows the arrangement of the locking means 11 in the overlapping region 10. The locking screw 27 has a flat head of larger diameter, an unthreaded stem portion 29, which has a smaller diameter and which forms the pivot pin for the connection of the free ends 8,9 in the overlapping region 10 of the transverse portions 5,7 of the side arms 2,3, and an immediately following threaded portion 28 which projects through the slot 23 in the E-shaped base plate 16. The locking nut 30 is preferably a knurled nut. A washer 31 is disposed between the slot 23 and the locking nut 30.

The base plate 16 also serves to support the bite fork 33, which is connected to the base plate 16 by means of a vertical rod 37, which is preferably screwed into the base plate, and of an adjustable horizontal rod 35. The bite fork 33 itself is adjustably connected to the horizontal rod 35 by means of a double clamp 36 acting on the bite fork handle 34. By inserting the bite fork handle into a depression 44 the surface of the bite fork can be kept flat, so that the upper jaw can be positioned freely. In the front region 46 the bite fork is preferably upwardly curved to correspond to anatomical configuration, as indicated schematically in FIG. 5. In order to prevent the double clamp 36 from slipping off the horizontal rod 35, the free end of the latter carries a screw 45 of plastics material, whose head has a diameter slightly greater than that of the horizontal rod 35.

In the regions of the pivot bearings 12,13 and of the locking means 11 between the base plate 16 and the transverse portions 5,7 it is preferable to provide respective plastic washers, preferably washers of polytetrafluoroethylene.

Each of the longitudinal portions 4,5 has a portion 38,39 bent over at an angle of about 90°, these portions 38,39 pointing towards one another. At the free ends of these bent-over portions 38,39 are provided so-called auditory canal inserts 40,41, which are intended for insertion into the auditory meatus of a patient (not shown) in order to establish the first reference plane. The bite fork 33 serves to establish the second reference point, while the third reference point is established by means of a spacer (not shown) which is mounted in the middle of the base plate 16 and which carries the nasion support.

When the locking means 11 is unlocked, the locking screw 27 and the locking nut apply no pressure forces to the base plate 16 and to the overlapping ends 8,9 of the transverse portions 5,7 of the side arms 2,3. The side arms 2,3 of the face bow 1 can now be moved around the pivot bearings 12,13, the locking screw moving along the longitudinal edges 24,25 in the overlapping region 10, following a slightly arcuate path of movement in the slot 23. Through this scissors-like movement of the side arms 2,3 around the pivot bearings 12,13, in conjunction with the movement of the locking means 11, the position of the two side arms 2,3 of the face bow 1 relative to each other is changed and thus enables the desired values to be taken from the head of the respective patient. When the face bow is removed from the patient's head, the adjusted position of the side arms of the face bow 1 must no longer be capable of variation. This purpose is served by the locking means 11 provided according to the invention. In order to lock the side arms in the adjusted position the locking nut 30 is screwed tight by two fingers on to the locking screw 27, which is non-rotatably seated in the transverse portion 5. The base plate 16 and the free ends 8,9 of the transverse portions 5,7 are thereby tightly pressed against one another, so that they are no longer freely movable relative to each other. Since the pivot pins 12,13 are only a very short distance from the locking means 11 in the overlapping region 10 it is ensured that during the manipulation of the face bow any contact made with the side arms 2,3 of the face bow 1 will result in practically no lever action, so that contact forces thus occurring will not be intensified and in particular will not be able to unlock the locking means 11.

List of References

1 Complete face bow
2 Right-hand side arm
3 Left-hand side arm
4 Longitudinal portion of 2
5 Transverse portion of 2
6 Longitudinal portion of 3
7 Transverse portion of 3
8 Free end of transverse portion 5
8a Crank at free end 8
9 Free end of transverse portion 7
9a Cutout at free end 9
10 Overlapping region
11 Locking means (complete)
12 Right-hand pivot bearing
13 Left-hand pivot bearing
14 L-bend of right-hand side arm 2
15 L-bend of left-hand side arm 3
16 E-shaped base plate
17 Outer E-leg of 16 (right hand)
18 Outer E-leg of 16 (left-hand)
19 End region of 17
20 End region of 18
21 Middle E-leg of 16
22 Connecting leg of 16
23 Slot
24 Right-hand parallel longitudinal edge
25 Left-hand parallel longitudinal edge
26 Longitudinal axis of face bow 1
27 Locking screw
28 Threaded portion of 27
29 Unthreaded stem portion of 27
30 Locking nut
31 Washer
32 Connecting line
33 Bite fork 34 Bite fork handle
35 Horizontal rod
36 Double clamp
37 Vertical rod mounted on base plate 16
38 Bent-over portion of 2 (right-hand)
39 Bent-over portion of 3 (left-hand)
40 Auditory canal insert (right-hand)
41 Auditory canal insert (left-hand)
42 Plastic washer
43 Plastic washer
44 Bite fork handle depression
45 Plastic screw
46 Front region of bite fork 33
47 Hole

I claim:

1. A face bow consisting essentially of two L-shaped side arms which are connected by pivot bearings to a base plate at two oppositely located peripheral pivot points for scissors-like movement, and which can be locked in the overlapping region of the ends of the transverse portions of the L-shaped side arms, wherein
   (a) the pivot bearings (12,13) are disposed in the respective L-bends (14,15) of the L-shaped side arms (2,3), and
   (b) in the middle between the pivot bearings (12,13) on which the base plate is mounted and spaced inwardly thereof, the base plate (16) is provided with a slot (23) in a portion of the plate which extends rearwardly of the remainder thereof whose longitudinal edges (24,25) extend parallel to the longitudinal axis (26) of the face bow (1) and through which projects the locking means (11), passing rotatably but non-slidably through the free ends (8,9) of the transverse portions (5,7) in the overlapping region.

2. A face bow as claimed in claim 1, wherein the free end (8) of the transverse portion (5) is cranked (8a).

3. A face bow as claimed in claims 1 or 2, wherein the locking screw (27) is fixedly seated in the free end (8) of the transverse portion (5) and passes through both the free end (9) of the transverse portion (7) and the base plate (16), without making contact with them, the free end (9) of the transverse portion (7) preferably having a cutout (9a) instead of a hole.

4. A face bow as claimed in claims 1, wherein respective plastic washers, preferably of polyamide, are disposed between the transverse portions (5,7) and the base plate (16) in the regions of the pivot bearings (12,13) and of the locking means (11).

5. A face bow as claimed in claims 1, wherein the base plate (16) is E-shaped, the pivot bearings (12,13) extend through the end regions (19,20) of the outer E legs (17,18) and the slot 23 is situated in the middle E leg (22).

6. A face bow as claimed in claim 1 or 5, wherein the outer E legs (17,18) extend at an obtuse angle to the connecting leg (22).

7. A face bow as claimed in claims 1, wherein the connecting leg (22) of the E-shaped base plate (16) serves to hold the bite fork (33).

* * * * *